United States Patent [19]

Kottenhahn et al.

[11] Patent Number: 5,387,696

[45] Date of Patent: Feb. 7, 1995

[54] REDUCTIVE AMINATION OF AN AMINO ACID OR OF AN AMINO ACID DERIVATIVE WITH AN α-KETO ACID OR AN α-KETO ACID DERIVATIVE

[75] Inventors: Matthias Kottenhahn, Hanau; Karlheinz Drauz, Freigericht; Horst Harr, Rodenbach, all of Germany

[73] Assignee: DeGussa Aktiengesellschaft, Frankfurt am Main, Germany

[21] Appl. No.: 912,684

[22] Filed: Jul. 13, 1992

[30] Foreign Application Priority Data

Jul. 13, 1991 [DE] Germany .................. 4123248

[51] Int. Cl.⁶ .................................. C07D 207/16
[52] U.S. Cl. ........................ 548/533; 560/24; 560/38; 560/159; 560/171
[58] Field of Search .............. 548/533; 560/24, 38, 560/159, 171

[56] References Cited

U.S. PATENT DOCUMENTS 4,474,692 10/1984 Oka et al. ................ 562/448 X

OTHER PUBLICATIONS

Article entitled "Synthesis and Pharmacology of the Potent Angiotensin-Converting . . . " J. Med. Chem. (1985) 28, 1596–1602, American Chemical Society; Johnson, et al.
Chemistry Letters, pp. 1691–1694, (1988) The chemical society of Japan; Iwasaki et al.

*Primary Examiner*—Joseph Paul Brust
*Attorney, Agent, or Firm*—Cushman Darby & Cushman

[57] ABSTRACT

N-substituted α-amino acids and dipeptides are valuable intermediate products for the production of inhibitors of the angiotensin converting enzyme (ACE); representatives are e.g. enalapril and ramipril. These compounds are prepared by means of hydrogenolytic conversion of a primary amine with a ketone with the addition of an organic or inorganic base; among the inorganic bases, basic aluminum oxide is preferred. The use of chiral organic bases favors the production of a diastereomer.

9 Claims, No Drawings

REDUCTIVE AMINATION OF AN AMINO ACID OR OF AN AMINO ACID DERIVATIVE WITH AN α-KETO ACID OR AN α-KETO ACID DERIVATIVE

The present invention relates to the reductive amination of an amino acid or of an amino acid derivative with an α-keto acid or an α-keto acid derivative in an inert solvent, in the presence of a hydrogenation catalyst and hydrogenation agent, as well as, optionally, with the removal of water. More particularly, the invention relates to such a method for producing compounds of the formula(I):

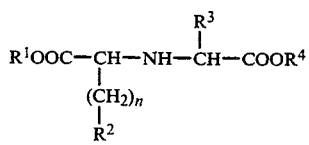

or of the formula II:

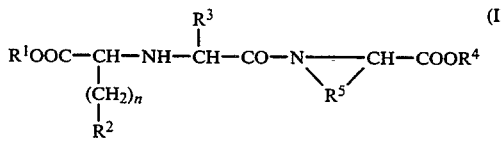

in which
$R^1$ signifies hydrogen, methyl-, ethyl- or benzyl, $R^2$ signifies hydrogen, $C_1$-$C_4$-alkyl, phenyl-or phenyl-($C_1$-$C_4$ alkyl ), $R^3$ signifies hydrogen, heteroalkyl- (e.g. group of a natural amino acid) or $C_1$-$C_4$-alkyl, benzyl-, 4'-hydroxybenzyl-, acylamino- ($C_1$-$C_5$) -alkyl-, tert. butyloxycarbonylamino-($C_1$-$C_5$) -alkyl-, benzyloxycarbonylamino- ($C_1$-$C_5$) -alkyl-, $R^4$ signifies H or an ester protective group, $R^5$ together with the atoms carrying it signifies a heterocyclic mono- or bicyclic ring system with 5 to 10 ring members
and
n signifies 0, 1 or 2, by means of hydrogenolytic conversion of a compound of the formula III

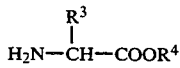

in which $R^3$ and $R^4$ have one of the meanings already indicated, in the case of preparation a compound of formula I, or through the hydrogenolytic conversion of a compound of the formula IV

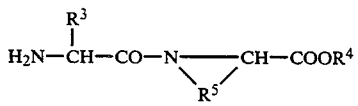

in which $R^3$ to $R^5$ have one of the meanings already indicated, in the case of preparation of compounds of formula II.

The hydrolyric conversion is carried out, in both cases, with a compound of formula V

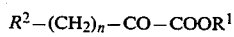

in which $R^1$, $R^2$ and n have one of the meanings already indicated, in the presence of an inert solvent, a hydrogenation catalyst, a hydrogenation agent and with optional removal of water.

The general terms such as "alkyl", "acyl", "aromatic", in the R groups also include such groups with typical substituents, such as 4-(trifluoroacetylamino)-butyl for $R^3$.

BACKGROUND OF THE INVENTION

N-substituted (α-amino acids (such as in formula I) and dipeptides (such as in formula II) containing them are valuable intermediate products for the production of inhibitors of the angiotensin converting enzyme (ACE) which are highly interesting as regulators of blood pressure. A few such N-substituted dimeprides are already commercially available as medicines or are in the registration stage, e.g. enalapril (N-[(S)-1-ethoxycarbonyl-3-phenylpropyl]-L-alanyl-L-proline), lisinopril (N-[(S) -1-carboxy-3-phenylpropyl]-L-lysyl-L-proline) or ramipril (2-[N-[(S)-1-ethoxycarbonyl-3-phenylpropyl]-L-alanyl]-(1S, 3S, 5S)-2-azabicyclo[3,3,0]-octane-3-carboxylic acid).

Such a method is described in J. Org. Chem. 1988, 53, pp. 836–844 for the production of compounds of formula II. Absolute ethanol serves as inert solvent, a molecular sieve for the removal of water and Raney nickel as hydrogenation catalyst. The products produced thereby are obtained in a 42–80 % yield according to the literature. However, these yields can be difficult to reproduce and, in addition, considerable amounts of byproducts usually remain in the products. This makes it difficult to purify them to pharmaceutically useful products.

A reductive amination of an amino acid ester with pyruvic acid is described in J. Med. Chem 28 (1985), pp. 1596–1602. The amino acid ester is used as hydrochloride. A small amount of NaOH is dissolved in the solvent, which liberates the amine from the amino acid ester hydrochloride and for the partial neutralization of the pyruvic acid. On the whole, there is an excess of acid in the reaction mixture, because of the pyruvic acid.

U.S. Pat. No. 4,474,692, especially examples 2, 7–14 and 21, teaches reductive aminations of dipeptides with α-keto acids. A buffer of sodium acetate and acetic acid is contained in the reaction mixture. The acetic acid is present the buffer in approximately double the molar excess.

SUMMARY OF THE INVENTION

The object of the present invention is to provide a modification of the known method which increases yields and which minimizes byproducts and which also minimizes expense. A further object is to provide such a method which enables the making of diastereoisomers, if desired.

These and other objects are achieved in a method in which the hydrogenolytic conversion is carried out in the presence of excess of an organic or inorganic base.

An excess of base is provided if the adducts used have been adjusted to their isoelectric point and then one or several compounds are still present in the system which decrease, in water, the hydrogen ion concentration of the water and/or which take up protons from water molecules, thus bringing about the formation of hydroxide ions, or, insofar as the pK value of the adducts used (their isoelectric point) is below pH 7, raising the pH in water above the pK value of the adducts.

The pH of the system (relative to the aqueous concentration) is preferably approximately at least 5.0 and advantageously approximately at least 6.0. Values of 6.2 and higher are especially suitable, with 11 and especially 10 being advantageous upper values.

This excess surprisingly clearly increases the chemical yield of the conversion even though the first step of the reaction, the imine formation (Roberts, J.D.; Caserio, M.C.; Basic Principles of Organic Chemistry, 2nd edition, W.A. Benjamin Inc., Philippines, 1977, pp. 697, 1154), is catalyzed by acid. Weak bases, such as organic bases such as mono-, di- or trierhanoi amine, trimethylamine, triethylamine, tripropylamine, tributylamine or N-methylmorpholine are especially suitable.

Suitable inorganic bases are salts of weak acids such as NaOAc, $K_2CO_3$, $KHCO_3$, $Na_2CO_3$ and, especially preferred, basic aluminum oxide.

Strong bases can also support the reaction, especially in very dilute concentration.

It is preferable if the excess base raises the (theoretical) pH of the reaction system only slightly above the pK value of the adducts. An elevation of 0.1 to 3, preferably 0.3 to 2 pH steps is customary.

The base is advantageously added in an amount of 0.01 to 5 molar equivalents, preferably from 0.05 to 2 molar equivalents relative to the amount of the compound of formula III or the compound of formula IV used. When using organic bases, hypostoichiometric amounts, especially 0.08–0.6 molar equivalents are particularly preferred.

The amino function of the amino acids or amino acid derivatives used must be present during the reaction at least partially in the form of a primary amine; this is also the case in the method of the present invention if this compound is used as an inner salt or otherwise as a salt, e.g. as hydrochloride.

The amino acid derivative is preferably an ester of an amino acid or an amide of the acid function; the amidic bonding preferably takes place with an additional amino acid or amino acid derivative so that the amino acid derivative is a di- or oligopeptide. On the whole, α-amino acids or their derivatives are preferred.

Compounds of formula V are particularly preferred in the form of α-keto acids or their derivatives, with pyruvic acid as the simplest representative.

The reaction usually requires the removal of the water produced. This can be achieved through the use of a water binding agent, preferably inert or basic. Suitable water binding agents are e.g. molecular sieves and aluminum oxides. The removal of water is particularly advantageous in the reaction of the keto group with the amine to the imine and is indicated in particular when using α-keto esters. Otherwise the reduction of the keto function as a side reaction could also possibly take place to a greater extent.

The addition of the organic base frequently makes it possible to distinctly reduce the amount of molecular sieve added as water binding agent and the addition of a basic aluminum oxide can render the molecular sieve quite superfluous because it functions itself simultaneously as a water binding agent. This reduces cost and minimizes by-products.

If an inorganic base, e.g. a basic aluminum oxide is used as an additive, this advantageously is used in an amount of 50 g/mole to 500 g/mole, relative to the amount of the compound of formula III or IV used, if the reaction water formed is to be bound with this base at the same time, otherwise in amounts of 2 to 400 g/mole.

The solvents used should preferably be anhydrous. Suitable inert solvents for the method of the invention are alcohols such as methanol, ethanol, propanol or butanol; ethers such as ethylene glycol dimethylether, diethylene glycol dimethylether or tetrahydrofuran; and carboxylic acid dialkylamides such as dimethylformamide or dimethylacetamide. Mixtures of such solvents can be used. It is advantageous if at least one protic solvent is used.

The hydrogenation catalysts and hydrogenation agents are preferably Raney nickel, palladium or palladium on activated carbon and platinum or platinum on activated carbon as well as $H_2$. If no stereoselectivity is desired, hydrides can also be used as hydrogenation catalysts and hydrogenation agents. Raney nickel is especially preferred since diastereoselectivity is best when it is used.

Among the diastereomers produced during the reaction, the S-configured product is usually preferred. The diastereoselectivity of the conversion required for the preferred production of the enantiomer can be increased even more, in many instances, if a chiral organic base is used. Such bases are, e.g., L- or D-prolinol, L- or D-valinol, (−)- or (+)-ephedrine and (−)- or (+)-norephedrine, which often increase the formation of an enantiomer, depending on the compounds used.

In the production of compounds of formula I, the naturally occurring α-amino acids or their optical antipodes, optionally in protected form, are preferred as compounds of formula III. Examples include are alanine, valine, methionine, cysteine, serine, tryptophane, asparagine, glutamine, aspartic acid, glutamic acid, phenylalanine, tyrosine, leucine, isoleucine or glycine and their esters, e.g. the benzyl-, tert. butyl- or ethyl esters (ester protective groups). If lysine or ornithine is used as the compound of formula III, the amino group in the side claim must be protected, such as by means of a trifluoroacetyl-, carbobenzoxy- or tert. butyloxycarbonyl group.

It can be advantageous during the conversion of compounds of formula III with a compound of formula V if they are first combined and heated with the aid of a suitable water-entraining solvent, such as cyclohexane, methyl-tert. butyl ether or toluene, to separate water and are azeotropically dehydrated in this manner. The compounds of formula III as well as of formula II can optionally also be used in the form of salts, e.g. as para toluene sulfonates or hydrochlorides, if $R^4$ does not signify H. In order to convert the salts into their free amines, the base should be present in a molar ratio of up to 100 mole % in the azeotropic dehydration. Weak bases such as N-methylmorpholine are preferred for this purpose. Care must be taken, in this procedure, that the formation of lactones or dimerization products of compound V is avoided, and high temperatures (especially above 100° C.) should also be avoided. If necessary, the solvent is subsequently changed and hydrogenolytically converted, that is, the base and the hydrogenation catalyst are added.

During the production of compounds of formula II, the following are preferably used as compounds of formula IV: Dipeptides from a naturally occurring α-amino acid or its antipodes, optionally protected in a possible side chain functionality, in the N-terminal position and from a cyclic (α-amino acid in the C-terminal position. Examples are alanyl-proline, $N^\epsilon$-trifluoroacetyl-lysyl-proline, $N^\epsilon$-carbobenzoxy-lysyl-proline, $N^\epsilon$-tert.butyloxycarbonyl-lysyl-proline, $N^\delta$-trifluoroacetyl-ornithyl-proline, $N^\delta$-carbobenzoxy-ornithyl-proline or $N^\delta$-tert.butyloxycarbonyl-ornithyl-proline.

2-oxo-4-phenyl-butyric acid ethyl ester is preferably used as the compound of formula V. The compounds of formula V are advantageously used in a 0.05 to simple [onefold] molar excess over the compound of formula III or IV.

In the practical execution of the method of the invention, a compound of formula V and a compound of formula III or IV are dissolved or suspended in the inert solvent. After the possible addition of a molecular sieve or aluminum oxide as a water binding agent, the organic or inorganic base (insofar as still necessary) is added. The reaction mixture is then advantageously pre-agitated for a time sufficient to bind any water still contained in it to the molecular sieve or to the basic aluminum oxide. The Schiff base also forms, during which time the water produced is likewise bound. After this preactivation, the previously dehydrated hydrogenation catalyst is added and the hydrogenolytic conversion is carried out under an atmosphere of hydrogen. An excess hydrogen pressure between 1 and 8 bars is especially preferred.

The method of the invention is especially advantageous in the case of reductive aminations which otherwise give no yields or only slight yields when catalyzed by acid (with an excess of acid) or at the isoelectric point (pK) of the adducts.

DETAILED DESCRIPTION OF PREFERRED EMBODIMENTS

The following examples illustrate the method of the invention in more detail:

EXAMPLE 1:

$N^\alpha$-[(S)-1-ethoxycarbonyl-3-phenylpropyl]-L-alanyl-L-proline 50 mmoles (9.3 g) Ala-Pro were suspended in 100 ml ethanol, mixed with 10 moles (1 g) triethylamine, 75 mmoles (15.5 g) 2-oxo-4-phenyl-butyric acid ethyl ester and 18 g molecular sieve 3 A and agitated for 2 hours under anhydrous conditions. One teaspoon of dehydrated Raney nickel and 15 g molecular sieve 3 A were now added, briefly reacted and subsequently hydrogenated for 22 hours under an atmosphere of 4 bars of $H_2$. The reaction mixture was filtered and evaporated to concentrate it to a small volume. Conversion (according to HPLC) relative to Ala-Pro used: 95.6%, product yield (according to HPLC): 95%. The residue was taken up in 250 ml ethanol and adjusted to pH 4.25 with conc. HCl (an aliquot was removed for this purpose, diluted with water and the pH adjusted, then the entire amount of HCl required was calculated). The solution was evaporated to low bulk under reduced pressure at 40° C. to 50 g, filtered with Celite and diluted to 100 ml total volume with ethyl acetate. 5.2 g maleic acid dissolved in ethyl acetate+ethanol were added and the mixture was seeded with enalapril maleate. The crystallizate formed was separated off and dried.

Yield: 20.9 g=85% of theory>99% SSS diastereomer, melting point: 145–146° C., $[\alpha]_D^{25}$: 42° (c=1 in MeOH).

Comparative Example $N^\alpha$-[(S)-1-ethoxycarbonyl-3-phenylpropyl]-L-alanyl-L-proline 50 moles (9.3 g) Ala-Pro were suspended in 100 ml ethanol, combined with 75 moles (15.5 g) 2-oxo-4-phenyl-butyric acid ethyl ester and 18 g molecular sieve 3 A and agitated for 2 hours under anhydrous conditions. One teaspoon of dehydrated Raney nickel and 15 g molecular sieve 3 A were now added, briefly reacted and subsequently hydrogenated for 22 hours under an atmosphere of 4 bars of $H_2$. The reaction mixture was filtered and evaporated to concentrate it to a small volume. Conversion (according to HPLC) relative to Ala-Pro used: 76.7%, product yield (according to HPLC): 35%. The residue was taken up is 250 ml ethanol and adjusted to pH 4.25 with conc. HCl (an aliquot was removed for this purpose, diluted with water and the pH was adjusted, then the entire amount was calculated). The solution was evaporated to low bulk under reduced pressure at 40° C. to 50 g, filtered by Celite and diluted to 100 ml total volume with ethyl acetate. 5.2 g maleic acid dissolved in ethyl acetate+ethanol were added and seeded with enalapril maleate. The crystallizate formed was separated off and dried.

Yield: 7.4 g=30% of theory,>99% SSS diastereomer, melting point: 145–146C, $[\alpha]_D^{25}$: 42° (c=1 in MeOH).

Example 2:

$N^\alpha$-[(S)-1-ethoxycarbonyl-3-phenylpropyl]-L-alanyl-L-proline

The same procedure was used as in Example 1; however, instead of triethylamine, 0.8 molar equivalent of ethanolamine were added as the base. Conversion (according to HPLC) relative to Ala-Pro: 85%, product yield (according to HPLC): 85%, diastereoisomer ratio before crystallization: SSS:RSS isomer=88.12

Example 3:

$N^\alpha$-[(S)-1-ethoxycarbonyl-3-phenylpropyl]-N-trifluoroacetyl-L-lysyl-L-proline 150 mmoles H-$N^\epsilon$-TFA-Lys-Pro-OH (50.9 g) were taken up in 120 ml n-butanol and approximately 50 ml n-butanol distilled off under vacuum. The solution was diluted with 500 ml ethanol. 22.5 g molecular sieve 3 A, 34 g 2-oxo-4-phenyl butyric acid ethyl ester and 30 mmoles triethylamine (4.2 ml) are added and the mixture agitated 2 hours under anhydrous conditions. Three teaspoons dehydrated Raney nickel were now added and the mixture was agitated for 4 hours at under an atmosphere of 4 bars of $H_2$. After this time, the pressure was released, another 12.4 g 2-oxo-4-phenyl butyric acid ethyl ester was added and the mixture was reagitated for 2 hours. Then a pressure of 4 bars of hydrogen was applied and the mixture was hydrogenated a further 4 hours at this pressure. The catalyst was separated off (it can be directly reused) and the solution was evaporated to a small volume. Conversion (according to HPLC) relative to $N^\epsilon$-TFA-Lys-Pro: approximately 95%, product yield (according to HPLC): 90%, diastereomer ratio: SSS:RSS-isomer=95.5. The residue was suspended in 450 ml water and 450 ml 1,1,1-trichloroethane at 5° C., the pH was adjusted to 9.6 in the aqueous phase with 50% NaOH and the phases were thoroughly mixed. The organic phase was separated off and the aqueous product phase was post-extracted with 100 ml 1,1,1-trichloroethane. The pH of 4.6 was now adjusted to 5 in the aqueous phase and this phase was extracted twice with 400 ml 1,1,1-trichloroethane. The organic phase was evaporated to low volume and taken up in 250 ml methyl-tert.butyl ether. The solution was cooled down to 0° C. and seeded. Yield: 48 g (60% of theory), SSS diastereomer content: >99%, $[\alpha]_D^{20}$: −25.5° [(c=1 in MeOH/ ·1N HCl (1:1)].

EXAMPLE 4

$N^\alpha$-[(S)-1-ethoxycarbonyl-3-phenylpropyl]-N-trifluoroacetyl-L-lysyl-L-proline The same procedure was used as in Example 4; however, instead of triethylamine, 0.2 molecular equivalent of tributylamine were added as the base. Conversion (according to HPLC) relative to $N^\epsilon$-TFA-Lys-Pro: 85%, product yield (according to HPLC): 75%, diastereomer ratio before crystallization: SSS:RSS diastereomer=96.4:3.6.

EXAMPLE 5

$N^\alpha$-[(S)-1-ethoxycarbonyl-3-phenylpropyl]-N-trifluoroacetyl-L-lysyl-L-proline The same procedure was used as in Example 4; however, instead of triethylamine, 0.8 molar equivalent ethanol amine were added as base. Conversion (according to HPLC) relative to $N^\epsilon$-TFA-Lys-Pro: 75%, product yield (according to HPLC): 65%, diastereomer ratio before crystallization: SSS:RSS diastereomer=93:7.

EXAMPLE 6

$N^\alpha$-[(S)-1-ethoxycarbonyl-3-phenylpropyl]-N-trifluoroacetyl-L-lysyl-L-proline The same procedure was used as in Example 4; however, instead of triethylamine, 0.2 molar equivalent L-prolinol were added as base.

Conversion (HPLC) relative to $N^\epsilon$-TFA-Lys-Pro: 85%, product yield (HPLC): 65%, diastereomer ratio before crystallization: SSS:RSS diastereomer=95:5.

EXAMPLE 7

$N^\alpha$-[(S)-1-ethoxycarbonyl-3-phenylpropyl]-N-trifluoroacetyl-L-lysyl-L-proline The same procedure was used as in Example 4; however, instead of triethylamine, 0.2 molar equivalent (1R,2S)-(−)-ephedrine were added as base. Conversion (according to HPLC) relative to $^\epsilon$-TFA-Lys-Pro: 84%, product yield (according to HPLC): 70%, diastereomer ratio before crystallization: SSS:RSS diastereomer=96.7:3.3.

EXAMPLE 8

$N^\alpha$-[(S)-1-ethoxycarbonyl-3-phenylpropyl]-N-trifluoroacetyl-L-lysyl-L-proline The same procedure was used as in Example 4; however, 0.1 molar equivalent triethylamine were added as base. Conversion (according to HPLC) relative to $N^\epsilon$-TFA-Lys-Pro: 75%, product yield (HPLC): 60%, diastereomer ratio before crystallization: SSS:RSS diastereomer=97.7:2.3.

EXAMPLE 9

$N^\alpha$-[(S)-1-ethoxycarbonyl-3-phenylpropyl]-N-trifluoroacetyl-L-lysyl-L-proline The same procedure was used as in Example 4; however, instead of molecular sieve and base, 25 g basic activated aluminum oxide were added. Conversion (according to HPLC) relative to $N^\epsilon$-TFA-Lys-Pro: 95%, product yield (HPLC): 80%, diastereomer ratio before crystallization: SSS:RSS diastereomer=95.5:4.5.

EXAMPLE 10

$N^\alpha$-[(S)-1-ethoxycarbonyl-3-phenylpropyl]-N-trifluoroacetyl-L-lysyl-L-proline The same procedure was used as in Example 4; however, instead of Raney nickel, palladium 1% on carbon was used as catalyst. Conversion (according to HPLC) relative to $N^\epsilon$-TFA-Lys-Pro: 90%, product yield (according to HPLC): 80%, diastereomer ratio before crystallization: SSS:RSS diastereomer=62:38.

EXAMPLE 11

$N^\alpha$-[(S)-1-ethoxycarbonyl-3-phenylpropyl]-L-alanine 250 mmoles L-alanine benzyl ester p-toluene sulfonic acid salt (88 g) and 312.5 mmoles 2-oxo-4-phenyl butyric acid ethyl ester (65 g) were suspended in 500 ml cyclohexane. After the addition of 250 mmoles N-methylmorpholine (25.3 g), water was removed by azeotropic distillation until the end of the reaction. After the mixture had cooled, it was filtered to remove salts, evaporated to low volume and taken up in 400 ml anhydrous methanol. After the addition of 25 mmoles N-methylmorpholine (1 g) and 3 teaspoons anhydrous Raney nickel, the mixture was hydrogenated at 4 bars excess hydrogen pressure and room temperature until the adsorption of hydrogen stopped. The reaction mixture was filtered from the catalyst, post-washed with warm methanol and evaporated to low volume. The residue was partitioned at 5° C. and pH 9.6 between water and 1,1,1-trichloroethane. The aqueous phase was subsequently extracted at pH 3 and 5° C. with 1,1,1-trichloroethane and the organic phase evaporated to low volume. The residue was crystallized from ethanol or acetone while cold.

Yield: 1st fraction: 35 g; 2nd fraction: 12 g

Melting point: 143–145° C.

What is claimed is:

1. In a reductive amination of an α-keto-compound selected from the group consisting of α-keto acids and α-keto acid derivatives of the Formula (V)

$$R^2-(CH_2)_n-CO-COOR^1 \quad\quad (V)$$

in which $R^1$ signifies hydrogen, methyl, ethyl or benzyl, $R^2$ signifies hydrogen, $C_1-C_4$-alkyl, phenyl or phenyl($C_1-C_4$-alkyl), and n signifies 0, 1 or 2, with an amino-compound of the Formula (III)

$$\underset{H_2N-CH-COOR^4}{\overset{R^3}{|}} \quad\quad (III)$$

in which $R_3$ signifies hydrogen, heteroalkyl-, or $C_1-C_4$ alkyl, benzyl-, 4'-hydroxybenzyl, acrylamino-($C_1-C_5$)-alkyl, tert.butyloxycarbonylamino-($C_1-C_5$)-alkyl, benzyloxycarbonylamino-($C_1-C_5$)-alkyl-, and $R^4$ signifies H or an ester protective group, or Formula (IV)

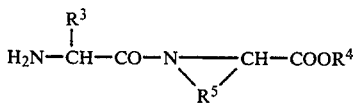

in which

R³ and R⁴ have one of the meanings already indicated and

R⁵ together with the atoms carrying it signifies a heterocyclic mono- or bicyclic ring system with 5 to 10 members in an inert solvent, and in the presence of a hydrogenation catalyst and a hydrogenation agent, both acting together to reduce a double bond in an intermediate formed by condensation of said keto-compound with said amino-compound to a single bond by incorporating hydrogen, so as to form a C-N bond between the C-atom of the keto-group of said keto-compound and the N-atom of the amino group of said amino-compound yielding a compound for Formula (I):

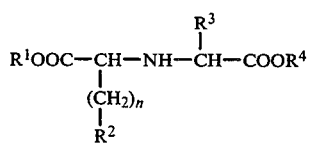

in which

R¹ to R⁴ and n have one of the meanings already indicated in the case that the compound of Formula (V) is reacted by means of hydrogenolytic conversion with a compound of Formula (III), or a compound of Formula (II):

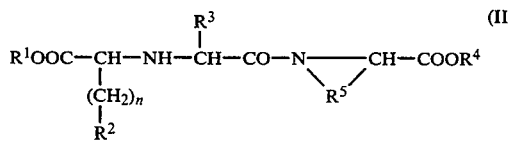

in which R¹ to R⁵ and n have one of the meanings already indicated in the case that the compound of Formula (V) is reacted by means of hydrogenolytic conversion with a compound of Formula (IV), as well as optionally removing water;

the improvement in which the reductive amination is carried out in the presence of an excess of base, an excess of base being provided if the adducts used have been adjusted to their isoelectric point and then at least one compound is still present in the system which decreases, in water, the hydrogen ion concentration of the water and/or which takes up protons from water molecules, or, if the pK value of the adducts used is below pH 7, which raises the pH of the water above the pK value of the adducts.

2. A method according to claim 1 in which mono-, di- or triethanol amine, trimethylamine, triethylamine, tripropylamine, tributylamine, N-methylmorpholine, L-or D-prolinol, L- or D-valinol, (−)- or (+)-ephedrine, (−)- or (+)-norephedrine are used as an organic base.

3. The method according to claim 1 in which $K_2CO_3$, $Na_2CO_3$, $KHCO_3$, NaOAc, $NaHCO_3$ or basic aluminum oxide are used as inorganic base.

4. The method according to claim 1 in which the base is added in an amount of 0.01 to 5 equivalents relative to the compound of formula III or IV used.

5. The method according to claim 4 in which the base is added in an amount of 0.05-2 equivalents relative to the compound of formula III or IV used.

6. The method according to claim 4 in which the base is an organic base and it is added in an amount of 0.08-0.6 molar equivalents relative to the compound of formula III or IV used.

7. The method according to claim 1 in which the basic aluminum oxide is added in an amount of 2 g/mole to 400 g/mole relative to the compound of formula III or IV added.

8. The method according to claim 1 in which basic aluminum oxide is added as a water binding agent for the removal of water.

9. The method according to claim 8 in which the basic aluminum oxide is added in an amount of 50 g/mole to 500 g/mole relative to the compound of formula III or IV added.

* * * * *